US009506901B2

(12) United States Patent
Lewis (10) Patent No.: US 9,506,901 B2
(45) Date of Patent: Nov. 29, 2016

(54) ADAPTABLE COMBINED CARBON MONOXIDE AND SMOKE DETECTOR (71) Applicant: William K. Lewis, Depew, NY (US)

(72) Inventor: William K. Lewis, Depew, NY (US)

( * ) Notice: Subject to any disclaimer, the term of this patent is extended or adjusted under 35 U.S.C. 154(b) by 0 days.

(21) Appl. No.: 14/633,531

(22) Filed: Feb. 27, 2015

(65) Prior Publication Data
US 2015/0247831 A1 Sep. 3, 2015

Related U.S. Application Data (60) Provisional application No. 61/945,865, filed on Feb. 28, 2014.

(51) Int. Cl.
*G01N 33/00* (2006.01)
*A45C 11/00* (2006.01)
*H02J 7/00* (2006.01)
*H04M 1/02* (2006.01)
*H02J 7/14* (2006.01)
*A45C 5/14* (2006.01)
*A45C 13/28* (2006.01)
*H04M 1/21* (2006.01)

(52) U.S. Cl.
CPC .............. *G01N 33/004* (2013.01); *A45C 5/14* (2013.01); *A45C 13/28* (2013.01); *H02J 7/1407* (2013.01); *H04M 1/21* (2013.01); *H02J 7/0042* (2013.01); *H02J 7/0054* (2013.01); *H02J 2007/0062* (2013.01); *H04M 2250/12* (2013.01)

(58) Field of Classification Search
CPC ...... A45C 13/28; A45C 5/14; G01N 33/004; H02J 2007/0062; H02J 7/0042; H02J 7/0054; H02J 7/1407; H04M 1/21; H04M 2250/12
See application file for complete search history.

(56) References Cited

U.S. PATENT DOCUMENTS

| 4,404,550 A * | 9/1983 | Shaw ..................... G08B 17/10 250/574 |
| 5,452,777 A * | 9/1995 | Giovannella ............ A45C 5/03 150/113 |
| 6,380,860 B1 * | 4/2002 | Goetz .................... G08B 25/10 340/539.1 |
| 2013/0221898 A1 * | 8/2013 | Frost ..................... H02J 7/1415 320/107 |

* cited by examiner

*Primary Examiner* — Kashif Siddiqui
(74) *Attorney, Agent, or Firm* — Del Vecchio and Stadler LLP (57) ABSTRACT A combined carbon monoxide and smoke detector adapted to fit into the handle of a suitcase or adaptable. The suitcase has wheels and the wheels are coupled to dynamos. Electric power generated by the dynamos is stored in a dynamo battery. The dynamo battery is wired to a charging port of a USB charger such that it is capable of charging the smoke and carbon monoxide detectors. In another embodiment there is a smartphone and a carbon monoxide sensor and a smoke sensor are built into the smartphone and make use of the internal components of the smartphone to sound an alarm is carbon monoxide or smoke are detected. The dock connector of the smartphone receives electrical energy from the dynamo battery to recharge the battery of the smartphone or other electronic device.

15 Claims, 8 Drawing Sheets

ADAPTABLE COMBINED CARBON MONOXIDE AND SMOKE DETECTOR

CROSS REFERENCE TO RELATED APPLICATION

This application claims the benefit of provisional U.S. Patent Application No. 61/945,865 filed on Feb. 28, 2014, the contents of which are hereby incorporated herein by reference.

FIELD OF INVENTION

This invention is directed to a combined carbon monoxide and smoke detector adaptable to fit into the handle of a suitcase or adaptable to fit on the reverse side of or internal to a smartphone or tablet or some other suitable electronic device. In another aspect, this invention is directed to a suitcase having wheels coupled to dynamos for generating electrical power.

BACKGROUND OF INVENTION

Recently, there has been an increase in incidents of carbon monoxide poisoning in the U.S. Symptoms of mild carbon monoxide poisoning include lightheadedness, confusion, headaches, vertigo, and flu-like effects. If the carbon monoxide exposure is longer, it can lead to significant damage to the central nervous system and heart. In some cases, the carbon monoxide poisoning has resulted in death. Carbon monoxide is colorless, odorless, tasteless, and initially non-irritating, thus it is very difficult for people to detect.

Carbon monoxide poisoning can be caused by a variety of different events. It may occur in the event of a faulty heating system, a faulty engine-driven generator or another faulty engine-driven tool, or may occur anywhere that there is combustion without adequate ventilation.

In the U.S., emergency rooms treat about 15,000 people per year for carbon monoxide poisoning and about 480 people per year die from carbon monoxide poisoning. Carbon monoxide poisoning has become such a problem that many jurisdictions require homes and apartments to have carbon monoxide detectors in addition to the standard smoke detectors. Notably absent from this requirement, hotels and motels are not required to provide carbon monoxide detectors in the rooms and thus many hotels and motels do not provide carbon monoxide detectors. As a result, in 2013, there were an estimated 750 carbon monoxide poisoning incidents in hotels and motels across the U.S.

While it is ultimately the responsibility of the hotel or motel to provide carbon monoxide detection and to ensure that the rooms are free of carbon monoxide, many travelers will not want to rely on the hotel or motel to provide carbon monoxide detection. Moreover, in cases of power outages, the hotels may be unable to detect carbon monoxide levels.

Another problem associated with traveling is that it is oftentimes very inconvenient or even impossible to gain access to an electric outlet in order to charge electronic devices such as cell and smart phones, tablets, and the like.

Thus, many travelers want the capability to monitor carbon monoxide in their hotel or motel room. Further, many individuals will want the capability to monitor carbon monoxide and smoke levels in non-hotel or motel settings. In addition, many travels want an easy, reliable and always available source of power to charge their electronic devices. Presently, there is no suitable portable carbon monoxide detector and smoke detector for use while traveling or for easy independent monitoring of carbon monoxide and smoke levels, nor is there a quick and reliable source of electric power that can be used to power these devices.

SUMMARY OF THE INVENTION

Accordingly, it is the subject of this invention to provide a portable carbon monoxide detector for quick, easy, and independent monitoring of carbon monoxide either during travel or in every day circumstances. In one embodiment, a combined carbon monoxide and smoke detector that is adapted to connect to the retractable handle of a suitcase is described. In another embodiment, a combined carbon monoxide and smoke detector adapted for use with a smartphone is described. In another preferred embodiment, the suitcase has dynamos that are coupled to the wheels of the suitcase. As the wheels rotate electrical energy is produced and stored in a dynamo battery. The stored energy is used to charge the batteries in the carbon monoxide and the smoke detector, and is used to power the smartphone battery disposed in any smartphone. The dynamo battery can serve as a power source for virtually any electronic device that has a need for electric energy or has rechargeable batteries.

DETAILED DESCRIPTION

A traditional carbon monoxide detector has a plastic housing and is typically mounted on a surface in a structure, for example the walls or ceiling of a building of house. Disposed internal to the plastic housing of the carbon monoxide detector is a silicon microchip that sends an electronic signal to the other components in the detector, including a sensor component. Often, the silicon microchip is fused to a copper-wired, integrated electronic circuit panel that is disposed on the plastic housing.

The carbon monoxide detector contains light-emitting diodes (hereinafter referred to as LEDs) to indicate whether the unit is functioning and whether the battery needs to be replaced. Some detectors also have a liquid crystal display (hereinafter referred to as LCD) panel that shows a read-out of carbon monoxide levels.

The carbon monoxide detector typically contains wires to the building's electrical system or has an internal battery to provide power to the detector. A test/reset button allows the user to make sure the alarm is working.

Within the plastic housing, there is a detection chamber that houses the carbon monoxide gas sensor. The carbon monoxide sensor identifies and measures carbon monoxide gas concentration in the atmosphere in parts per million (hereinafter referred to as ppm). An alarm is also disposed within the plastic housing and the alarm is capable of producing and 85 decibels audible sound. When the carbon monoxide sensor detects dangerous levels of the gas, it sends an electronic pulse to the alarm thus activating the alarm. A typical dangerous threshold for the carbon monoxide concentration is seventy (70) ppm. Thus, once the concentration of carbon monoxide reaches 70 ppm, the carbon monoxide sensor will cause the alarm to sound.

Carbon monoxide detectors can use several different types of carbon monoxide sensor components to sense carbon monoxide in the air. The carbon monoxide sensor component may be a biomimetic sensor or a metal oxide semiconductor sensor or an electrochemical sensor. The batteries and carbon monoxide sensor components of carbon monoxide detectors need to be replaced every seven to ten years.

Smoke detectors are variously made, for example some smoke detectors include smoke detector sensor components that are optical detectors having a light sensor that includes light source, a lens and photoelectric receiver, while other smoke detector sensor components have ionizing type smoke detector sensor components. Smoke detectors may be wired to the power source of a building or may be battery powered.

Figure 1:
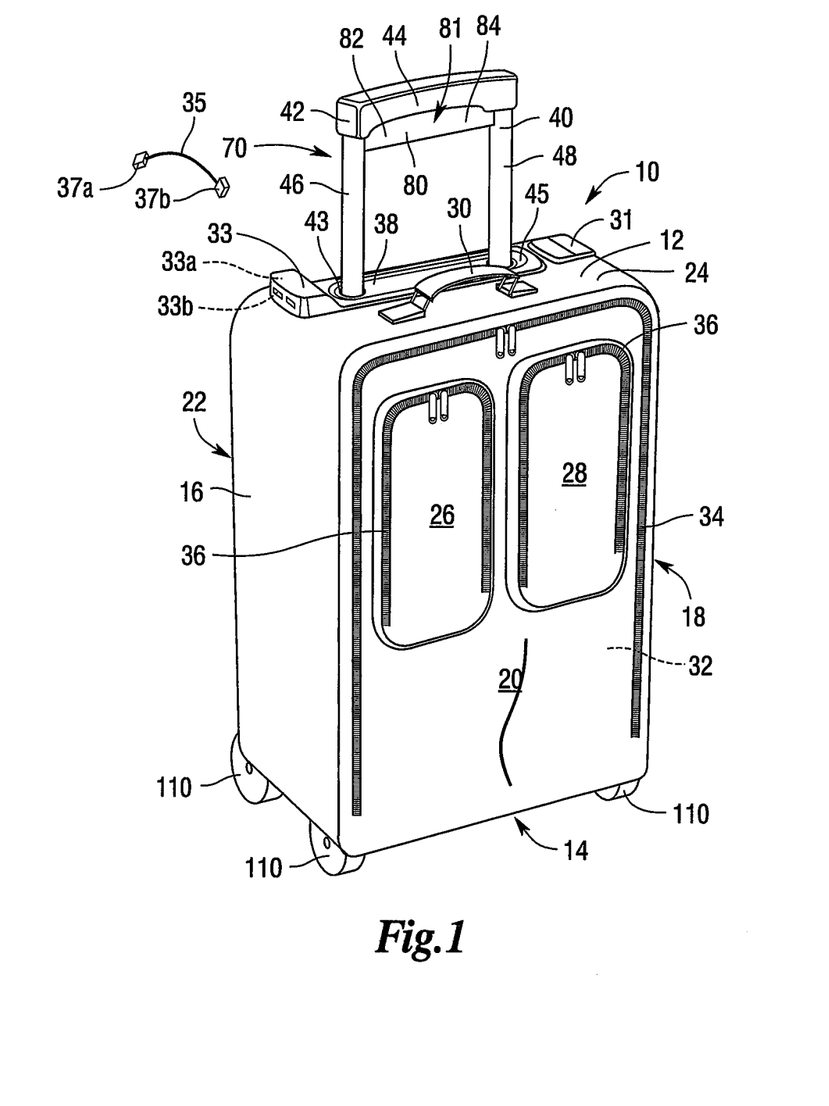
FIG. 1 is a perspective view of a suitcase having a carbon monoxide and smoke detector.
Figure 2:
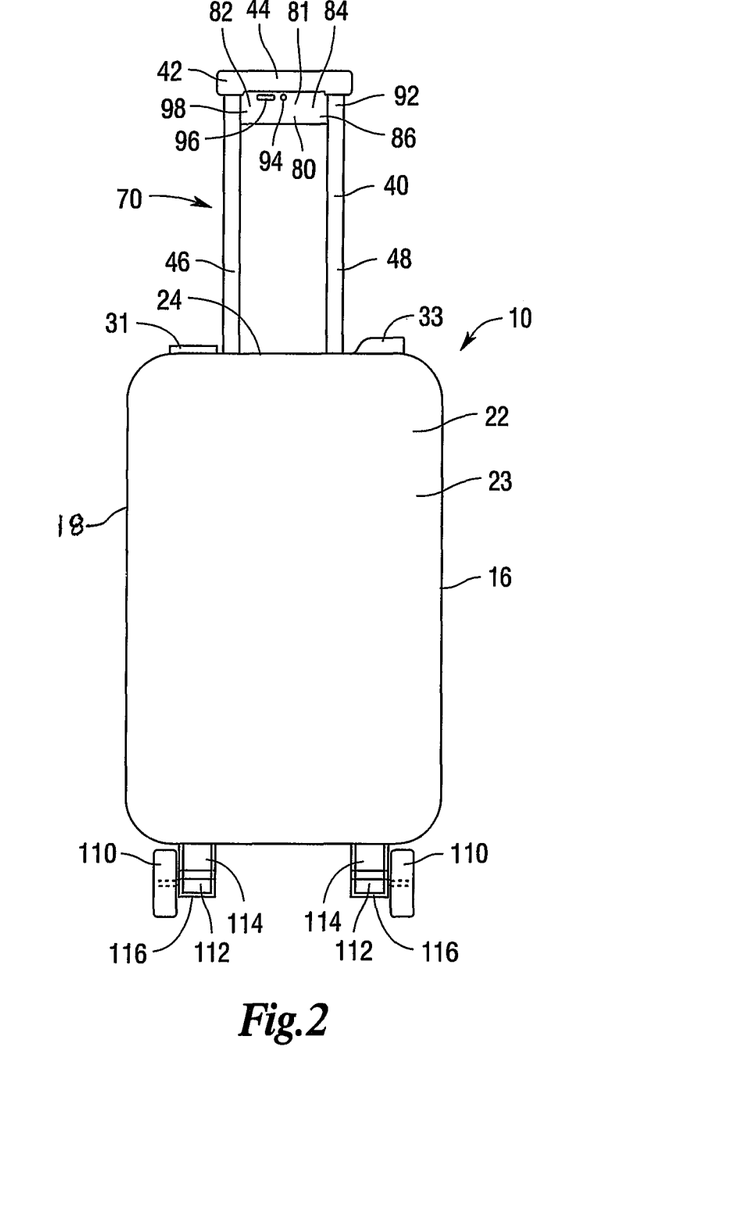
FIG. 2 is a rear view of the suitcase having a carbon monoxide and smoke detector

As shown in FIG. 1, there is a suitcase 10 having a suitcase housing 12. The suitcase housing 12 may have a generally rectangular shape as shown. The suitcase housing has a suitcase housing base 14. Extending from the suitcase housing base 14 are opposed first and second suitcase housing sides 16, 18 that are flat in one of the preferred embodiments. Also extending from the suitcase housing base 14 are a suitcase housing access side 20 and an opposed suitcase handle side 22 (FIG. 2). The first and second suitcase housing sides 18, 20 and the suitcase housing access side 20 and the opposed suitcase handle side 22 are joined to a suitcase housing end 24, such that the suitcase housing end 24 and the suitcase base housing base 14 are opposed to one another.

Figure 8:
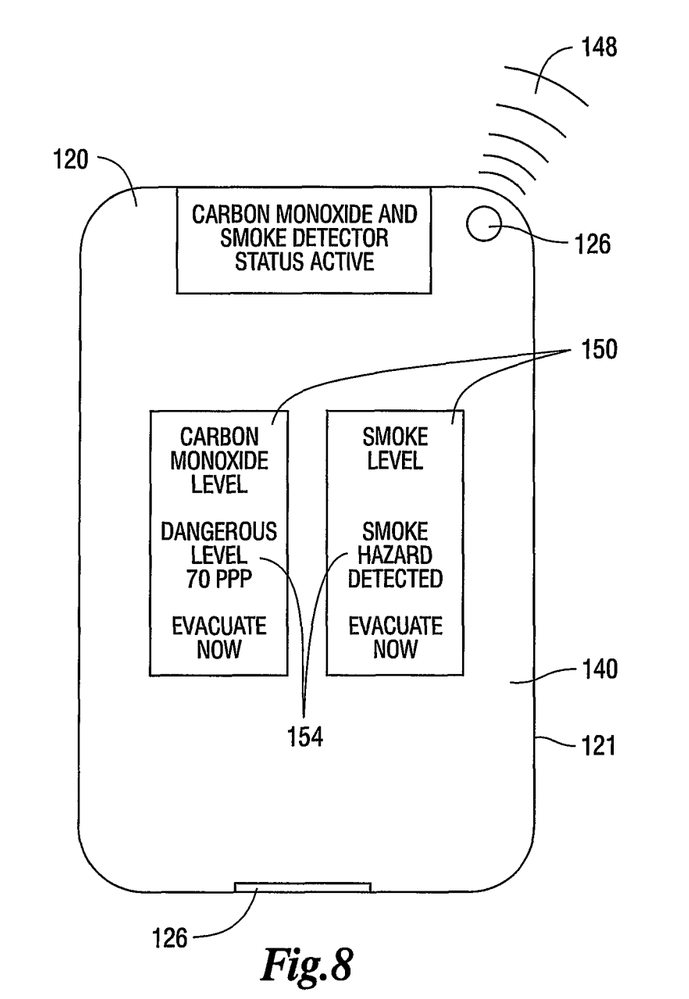
FIG. 8 is a screen display of the smart phone indicating the status of carbon monoxide and smoke levels.

The suitcase housing access side 20 has mounted thereon first and second side pockets 26, 28, and the suitcase housing end 24 has mounted thereon a carry handle 30 and an electronic device pocket 31. Also mounted on the suitcase housing end 24 is a charger 33. In one of the preferred embodiments the charger 33 is a universal serial bus (USB) charger 33a with a charging port 33b. The USB charger 33a is capable of charging electronic devices, for example smartphones 120 as will be described presently. A cable 35 having first and second connectors 37a, 37b at its ends is provided. The first connector 37a can be plugged into the charging port 33b of the USB charger 33a, and the second end 37b can be plugged into an electronic device, for example a smartphone dock 126 (FIG. 8). Electronic device ports and docks, USB chargers and ports and cables for use with such ports are well known to those having ordinary skill in the art and are therefore not described in greater detail herein. It is pointed out that the electronic device pocket 31 can be sized such that it is capable of housing various electronic devices other than smartphones 120. In addition, mounted on the suitcase housing end 24 is a handle guide 38 having a handle guide opening 43 that leads to a handle recess 45 that is defined in the suitcase 10. The suitcase housing 12 also defines a suitcase housing interior 32 that is accessed by way of a housing zipper 34. The first and second side pockets 26, 28 can be accessed with pocket zippers commonly designated 36.

Figure 3:
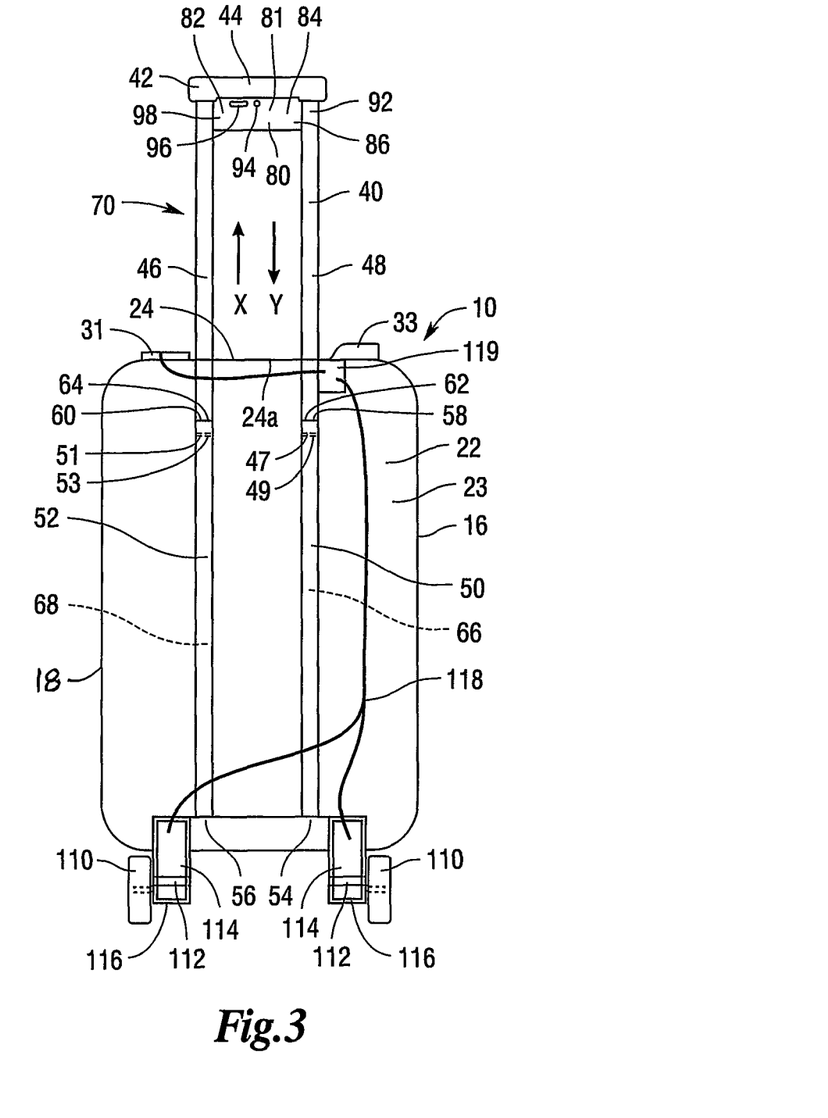
FIG. 3 is a rear view of the suitcase having a carbon monoxide and smoke detector depicts wherein a handle assembly is exposed.
Figure 4:
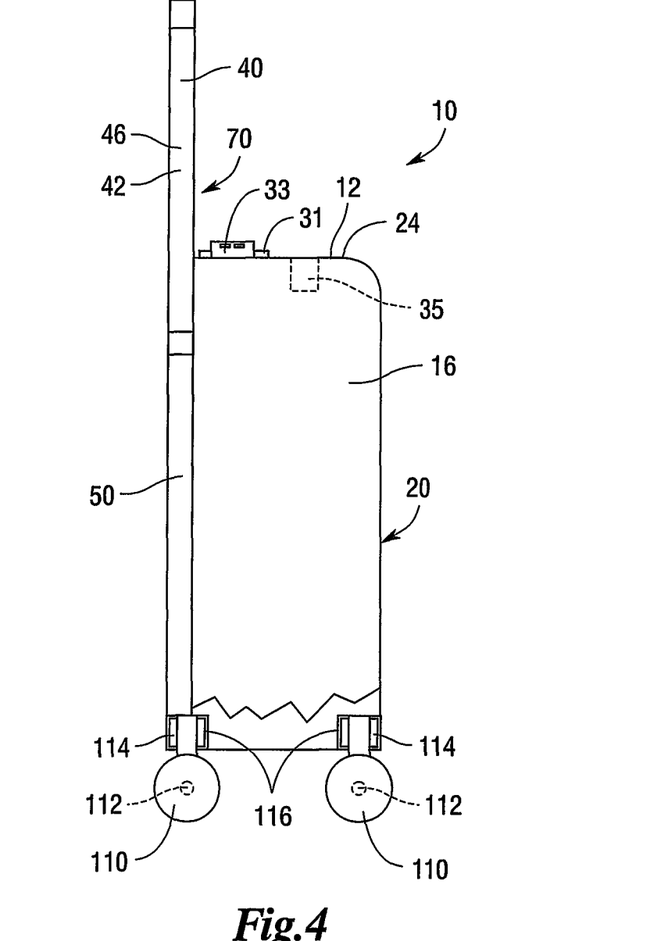
FIG. 4 is a left side view of the suitcase having a carbon monoxide and smoke detector.

As best shown in FIG. 2, the suitcase handle side 22 has a cover layer 23. FIG. 3 shows the suitcase handle side 22 wherein the cover layer 23 is not present to expose a handle assembly 40. The handle assembly 40 includes a handle 42 that has a handgrip portion 44 that is capable of being manually gripped by a user. In one preferred embodiment, the handgrip portion 44 is straight and in other preferred embodiments the handgrip portion 44 may be curved.

The handle 42 also includes also includes a first and second slider arms 46, 48 that are connected to and extend from the handgrip portion 44 of the handle 42. The first and second slider arms 46, 48 are parallel to one another and are structurally the same in one of the preferred embodiments. The first slider arm 46 has a first slider arm distal end 47 from which extends first slider arm engagement member 49, and the second slider arm 48 has a second slider arm distal end 51 from which extends second slider arm engagement member 53.

Figure 5:
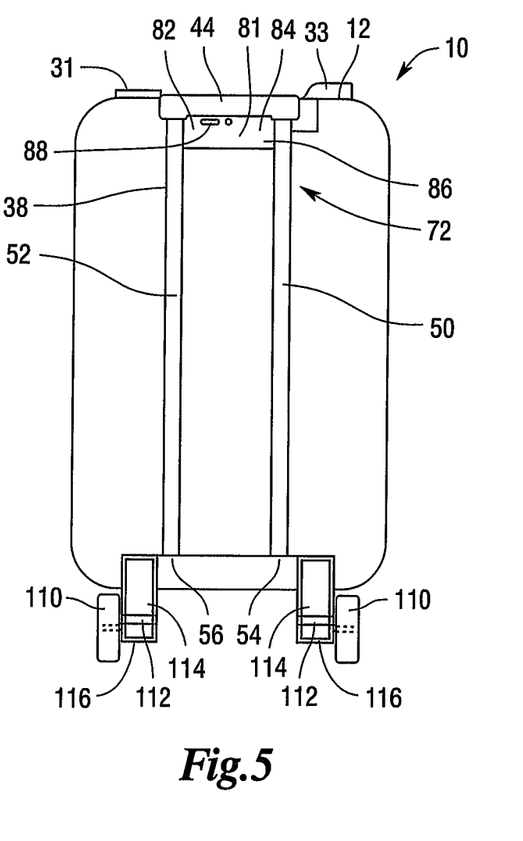
FIG. 5 is a rear view of the suitcase having a carbon monoxide and smoke detector wherein the handle is in a retracted handle position.

As shown in FIG. 3, the handle assembly 40 also includes first and second slider receiving members 50, 52 that are mounted to the suitcase 10. Each of the first and second slider receiving members 50, 52 has a closed end 54, 56 respectively, and an opposed open end 58, 60, and have stop walls 62, 64 that extend into the open ends 58, 60. Each of the first and second slider receiving member 50, 52 also defines a slider cavity 66, 68. The first and second slider arms 46, 48 are disposed in the first and second slider receiving member 50, 52, respectively, such that they can be slid in the direction of the arrow designated X and moved out of the slider receiving member 50, 52, and can be moved in the direction in the arrow designated Y and slid into the first and second slider receiving members 50, 52. The first and second slider arms 46, 48 are prevented from exiting the first and in the first and second slider receiving members 50, 52 members due to the first and second slider arm engagement portions 49, 53 engaging the stop walls 62, 64. Thus, the handle 42 is movable from an extended handle position 70 (shown in FIGS. 1-4) to a retracted handle portion 72 (shown in FIG. 5).

FIGS. 1-3 and 5 show a portable combined carbon monoxide detector and smoke detector 80. The portable combined carbon monoxide detector and smoke detector 80 has a detector housing 81 and disposed internal to the detector housing is a carbon monoxide detector 82 and a smoke detector 84. The detector housing 81 is made of plastic in one of the preferred embodiments, but may also be made of metal and other suitable materials.

Figure 6:
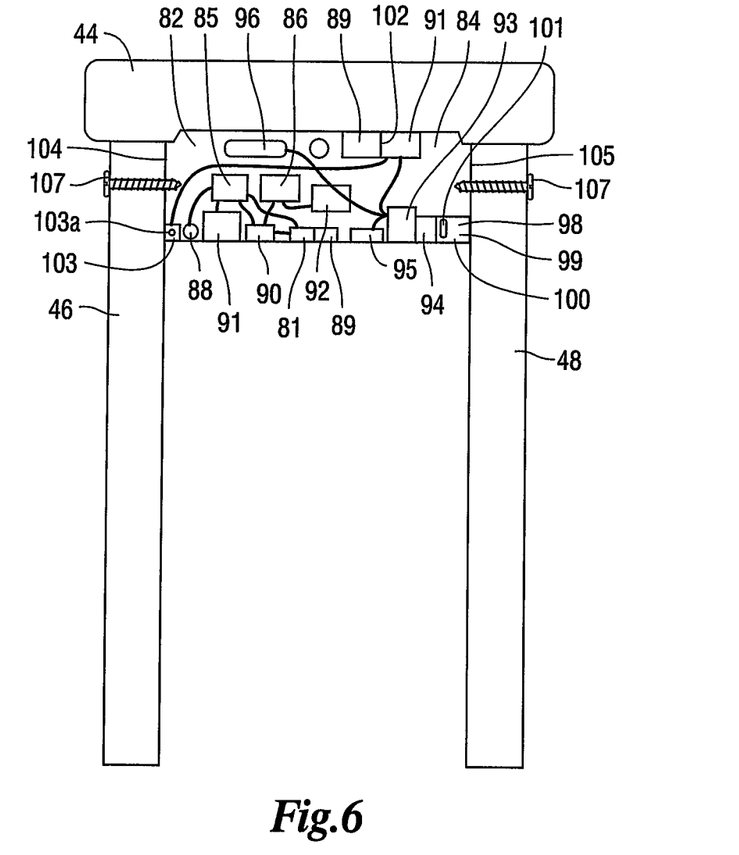
FIG. 6 is an enlarged view of the detector housing and components housed therein.

As shown in FIG. 6, the carbon monoxide detector 82 includes the components that are found in a standard or known carbon monoxide detectors including a silicon microchip 85 that is capable of sending a charge to an integrated electronic circuit panel and associated wiring, an LED to indicate to the user that the carbon monoxide detector 82 is functioning or requires batteries 91, a test button 88, an alarm 89 that may be an audible alarm, a liquid crystal display (LCD) panel 90 that displays a readout of the carbon monoxide level, a battery 91, and a carbon monoxide sensor component 92 that may be embodied as a biomimetic sensor or a metal oxide semiconductor sensor or other carbon monoxide sensors described herein or known to those having ordinary skill in the art. In another preferred embodiment the carbon monoxide sensor component 92 may be embodied as an electrochemical sensor. The construction, use and operation of carbon monoxide detectors are well known to those having ordinary skill in therefore the carbon monoxide detector is not described in greater detail herein.

The smoke detector 84 includes the components found in a standard smoke detector or known smoke detectors including a microchip and associated circuitry and wiring 93, a LED to indicated to indicate the smoke detector 94 is functioning, an alarm 95, a test button 96, a battery 91 and a smoke sensor component 98. The smoke sensor component 98 includes a smoke chamber 99, a light source 100, for example an LED, a photoelectric receiver 101, for example a photodiode. The battery 91 powers the smoke detector 84 and its associate components. Smoke enters the smoke chamber 99 and its presence causes a change in the light received by the photodiode that is detectable and that causes the alarm 95 to sound. A separator wall 102 may be present internal to the detector housing 81 that separates the carbon monoxide detector 82 from the smoke detector 84. Smoke detectors and the construction, use and operation of smoke detectors are well known to those having ordinary skill in therefore the smoke detector is not described in greater detail herein.

It is pointed out that a single battery 91 may be used to power both the carbon monoxide detector 82 and the smoke detector 84. In addition, the portable combined carbon monoxide detector and smoke detector 80 has a detector charger 103 having a detector charging port 103a. The detector charger 103 is mounted on the detector housing 81 and it is wired to the battery 91 or batteries such that they can be recharged. The batteries 91 mentioned above are rechargeable batteries or may be non-rechargeable batteries in other preferred embodiments. Thus, for embodiments wherein the batteries are rechargeable batteries, for example lithium-ion type batteries, they can be charged via the detector charging port 103a.

The detector housing 81 also has opposed first and second detector housing ends 104, 105, and first detector housing end 104 is mounted to the first slider arm 46, and the second detector housing end 105 is mounted to the second slider arm 48, such that the portable combined carbon monoxide detector and smoke detector 80 is supported by the first and second slider arms 46, 48 and moves with the handle assembly 40. In addition, in another preferred embodiment the portable combined carbon monoxide detector and smoke detector 80 may be inserted into and supported by the handgrip portion 44 of the handle 42. As shown, the a portable combined carbon monoxide detector and smoke detector 80 is perpendicular to the first and second slider arms 46, 48 in one of the preferred embodiments.

The mounting may be with screws 107 that extend through the first and second slider arm 46, 48, respectively and into the detector housing 81, such that the detector housing 81 is easily removed for maintenance. The mounting may also be accomplished with only one screw 107. In yet other preferred embodiments the portable combined carbon monoxide detector and smoke detector 80 may be supported by the first and second slider arms 46, 46 by way of a pressure fit or pressure and friction fit with the first and second slider arms 46, 48. In addition, in one of the preferred embodiments portable combined carbon monoxide detector and smoke detector 80 is mounted such that the detector housing 81 abuts against the handgrip portion 44 of the handle assembly 40. The portable combined carbon monoxide detector and smoke detector 80 is adapted for use with existing suitcases 10 and may installed in suitcases at the point of manufacture.

In addition, it is pointed out that the placement of the portable combined carbon monoxide detector and smoke detector 80 on the first and second slider arms 46, 48 allows the portable combined carbon monoxide detector and smoke detector 80 to retract when the first and second slider arms 46, 48 retract, such that the portable combined carbon monoxide detector and smoke detector 80 is in an out of the way position (FIG. 5) when the handle 42 is in the retracted handle portion 72 and will not interfere with the use and operation of the suitcase 10.

In other preferred embodiments the portable combined carbon monoxide detector and smoke detector 80 may be sized and configured fit within and be supported by the first and second slider arms 46, 48 of variously sized existing suitcases 10 or newly build suitcases.

As shown in FIGS. 1-5 the suitcase 10 also has four wheels commonly designated 110. Shafts 112 extend through and are connected to the wheels 110 such that as the wheels 110 rotate the shafts 112 also rotate. Each of the shafts 112 also extends into a dynamo 114 and the dynamos 114 have dynamo housings 106. The shafts 102 are coupled to the dynamos 104. Dynamos and the use, operation and construction of dynamos are well known to those having ordinary skill in the art and therefore the dynamos are not described in greater detail herein. As shown in FIG. 3, a wire 118 extends from each dynamo 114 and through the dynamo housings 116. As the wheels 110 and shafts 112 rotate the dynamos 114 generate electricity, for example direct current electricity. The wire 118 delivers the electric power generated by the dynamos 114 to a dynamo battery 119 such that as the user pulls the suitcase 10 the electricity generated is delivered to and stored in the dynamo battery 119. The dynamo battery 119 is a rechargeable battery, for example a lithium ion type rechargeable battery and may be mounted to an inner side 24a of the suitcase housing end 24. The dynamo battery 119 is wired to the USB charger 33a such that electrical energy can be delivered from the charging port 33b to electronic devices powered by electricity as previously described. For example, the cable 35 can deliver electrical energy to the smartphone 120 or other electronic device. Thus, as the user pulls or pushes the suitcase 10 the wheels 110 rotate and that causes the dynamos 114 to generate electricity that can be delivered by the wire 118 to a dynamo battery 119 and the electrical energy is stored in the dynamo battery 119. This allows the user to plug into the USB charger 33a whenever power is needed. In other preferred embodiments at least one wheel 110 is connected to a dynamo 114, or in embodiments wherein the suitcase 10 only has two wheels 110 each wheel 110 may be connected to a dynamo 114. Thus, as a user moves the suitcase 10 and the wheels 110 roll electric energy is generated and stored in the dynamo battery 119.

The dynamo battery 119 can be used to charge the battery 91 (or batteries 91) of the carbon monoxide detector 82 and the smoke detector 84. In particular, The first connector 37a of the cable 35 is be plugged into the charging port 33b of the USB charger 33a and the second connector 37b is plugged into the detector charging port 103. Thus, the user can charge the battery 91 in the carbon monoxide detector 82 and the smoke detector 84 whenever he or she desires.

In addition, the dynamo battery 91 may be used to supply power to other electronic devices, for example cameras, tablets, personal digital assistants, and other devices in need of electrical energy.

Figure 7:
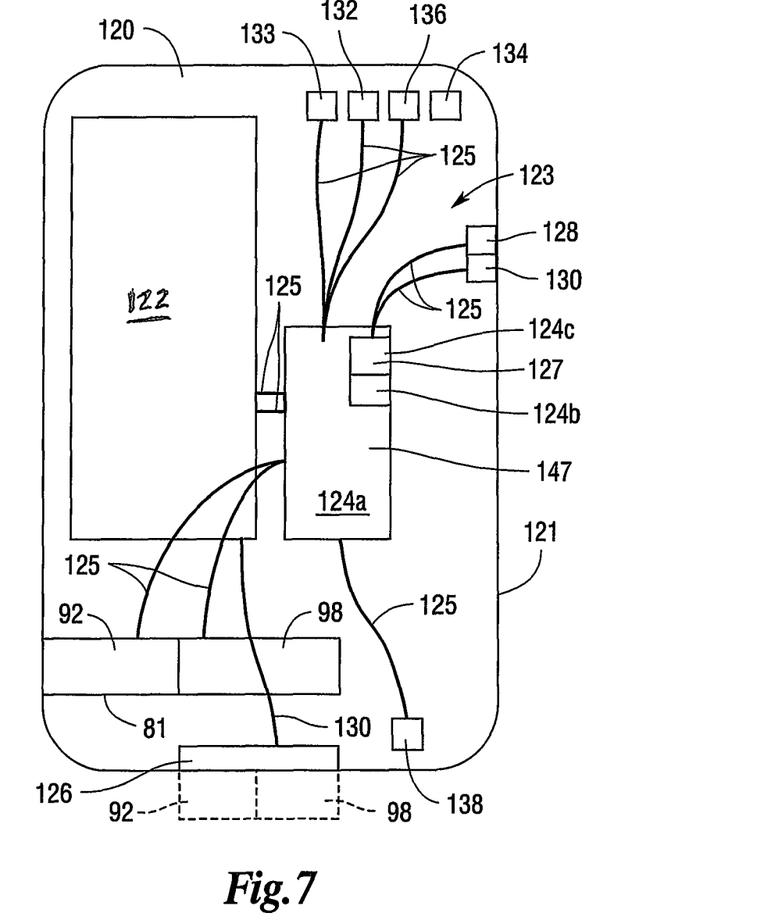
FIG. 7 is a front view of a smart phone wherein the screen display of the smart phone has been removed.

As shown in FIGS. 7 and 8, in another embodiment preferred embodiment, the portable combined carbon monoxide detector and smoke detector 80 is adapted for use with a smartphone 120 or other electronic device now known or developed in the future, and makes use of the components that already exist in the smartphone 120. FIG. 7 shows the smartphone 120 and it has a smartphone housing 121 on which is mounted a screen display 140 (FIG. 8). The screen display is removed in FIG. 7. The screen display 140 may be embodied as a LCD screen display. The smartphone 120 includes internal components 123 including a smartphone battery 122, a smartphone computer 124a having a smartphone central processing unit 124b and a smartphone memory component 124c, associated smartphone circuitry and wires 125, a dock connector 126 that can serve as a charging port, volume and power buttons 128, 130, a camera 132, LEDs 133, an antennae 134, a speaker 136 capable of broadcasting noise and alarms, and a vibrator 138 all under the control of the smartphone computer 124a. The smartphone battery 122 is a rechargeable lithium type battery in one of the preferred embodiments. The LCD screen display 140 shown in FIG. 8 and is capable of emitting alarms, visual messages and status reports, and light. Smartphones and the use, construction, and operation of smartphones 120 and other electronic devices are well known to those having ordinary skill in the art and are therefore not described in greater detail herein.

In addition, the smartphone 120 also had disposed therein the above-described carbon monoxide sensor component 92 and the smoke sensor component 98 that are in communication with the smartphone computer 124a and its associated circuitry and wires 125. The LEDs 133, the screen display 140, smartphone battery 122, and audible alarms emitted from the speaker 136 of the smartphone 120 are utilized to alert a user of dangerous carbon monoxide and/or smoke levels. In this embodiment, carbon monoxide sensor component 92 and a smoke sensor component 98 are in communication with smartphone 120.

The carbon monoxide sensor component 92 and a smoke sensor component 98 are capable of communicating with components of the smartphone 120 by way of a downloadable application 147 that connects and allows communication between the carbon monoxide sensor component 92 and the smoke sensor component 98 and the smartphone 120. The carbon monoxide sensor component 92 and a smoke sensor component 98 output signals that are processed by the smartphone 120 to alert the user with audible alarms 148, visual printed indicia warning information 150 (FIG. 8), and/or lights and flashing lights when either carbon monoxide or smoke are detected or exceed predetermined levels. For example and as shown in FIG. 8, if dangerous levels of carbon monoxide and/or smoke are detected, then the screen display 140 displays printed indicia warning information 154 providing the status of the carbon monoxide and smoke detectors 82, 84 and displays the carbon monoxide and smoke levels are at a dangerous or hazardous level and for the user to evacuate now. Writing applications for use in connection with smart phones, such as the downloadable application 127 described herein, for and similar electronic devices is well known to those having ordinary skill in the art and therefore is not described in greater detail herein.

In use, when the carbon monoxide sensor component 92 and a smoke sensor component 98 are connected by the smartphone circuitry and wires 125, the smartphone 120 runs the downloadable application 147 and activates the carbon monoxide sensor component 92 and a the smoke sensor component 98 with the smartphone battery 122 providing the electricity. LED's 133 emit light and/or an audible beep is generated or other form of an alarm, or lights are emitted from the smartphone 120 to indicate that the carbon monoxide sensor component 92 and a smoke sensor component 98 are functioning properly. The screen display 140 of the smartphone 120 serves as the LCD display to indicate the carbon monoxide level and or smoke level as shown in FIG. 8 when the downloadable application 147 is running. As the carbon monoxide level and smoke levels are determined by the carbon monoxide sensor component 92 and a smoke sensor component 98 this information or data is communicated to the downloadable application 147. In the event that a dangerous amount of carbon monoxide and/or smoke is/are detected, that is the levels of carbon monoxide and smoke exceed predetermined threshold levels, the downloadable application 147 will output signals causing the screen display 140 (FIG. 8) to display warning messages and sound light and sound alarms as described above.

It is pointed out that the dynamo battery 119 can be used to charge the smartphone battery 122 or the battery of virtually any electronic device. The first connector 37a of the cable 35 is plugged into the charging port 33b of the USB charger 33a and the second connector 37b is plugged into the dock connector 126 of the smartphone 120 or other electronic device. Thus, the user can charge the smartphone battery 122 or any electronic device whenever he or she desires as there is always a supply of electric energy stored in the dynamo battery 119 because the dynamo battery 119 is always being recharged as the suitcase 10 pulled and the wheels 110 roll.

In yet another preferred embodiment, the carbon monoxide sensor component 92 and a smoke sensor component 98 are mounted to the smartphone housing 121 and are external to the smartphone 120 are adapted to plug into the dock connector 126 such that they are in communication with the smartphone 120 and send signals to the smartphone 120 including carbon monoxide and smoke levels.

In another embodiment, the carbon monoxide sensor component 92 and a smoke sensor component 98 are mounted on a tablet, laptop, or other electronic device. The downloadable application 127 is downloaded to the tablet, laptop or other electronic device and the carbon monoxide sensor component 92 and a smoke sensor component 98 make use of the internal components of the tablet, laptop or other electronic device to alert the user when dangerous levels of smoke or carbon monoxide are detected in the manner described above in connection with the smartphone 120.

It is pointed out that the in other preferred embodiments the dynamo battery 119 can be used to power virtually any electronic device, and the carbon monoxide sensor component 92 smoke sensor component 98 can be build into virtually any electronic device.

In other preferred embodiments only one of the carbon monoxide detector 82 and the smoke detector 84 are present in the embodiments described above.

It will be appreciated by those skilled in the art that while the combined carbon monoxide and smoke detector 80 for use with of the suitcase 10 and adapted for use with the smartphone 120 and other electronic devices, and the dynamo 104 for providing power have been described in detail herein, the combined carbon monoxide and smoke detector 80 for use with the suitcase 10 and adapted for use with a smartphone 120, and the dynamo 104 for providing power, and associated embodiments are not necessarily so limited and other examples, embodiments, uses, modifications, and departures from the described embodiments, examples, and uses may be made. All of these embodiments are intended to be within the scope and spirit of the combined carbon monoxide and smoke detector 80 for use with of a suitcase 10 and adapted for use with the smartphone 120, and the dynamo 104 for providing power.

What is claimed:

1. A portable combined carbon monoxide detector and smoke detector comprising:
   a detector housing;
   a carbon monoxide detector disposed in the detector housing;
   a smoke detector disposed in the detector housing;
   a suitcase having a suitcase housing and a handle assembly supported by the suitcase housing and the handle assembly includes a handle with a handgrip portion and the handle having first and second slider arms that extend from the handgrip portion and wherein the detector housing is mounted on the first slider arm.

2. The portable combined carbon monoxide detector and smoke detector according to claim 1 wherein the handle assembly further includes first and second slider receiving members that are mounted to the suitcase and wherein the first slider arm is received in the first slider receiving member and the second slider arm is received in the second slider receiving member such that the first and second slider arms can be slid into and out of the first and second slider receiving members.

3. The portable combined carbon monoxide detector and smoke detector according to claim 2 wherein the detector housing abuts the handgrip portion and the detector housing is extendable from the first and second slider arms.

4. The portable combined carbon monoxide detector and smoke detector according to claim 1 wherein the suitcase housing has a housing base and opposed first and second suitcase housing sides that extend from the housing base, a suitcase housing access side and an opposed suitcase handle side that extend from the housing base, and a suitcase housing end joined to the opposed first and second suitcase housing sides and joined to the opposed suitcase housing access side and the suitcase handle side such that the suitcase housing end is opposite the housing base and wherein an electronic device pocket is connected to the suitcase housing end and a charger is mounted on the suitcase housing end.

5. The portable combined carbon monoxide detector and smoke detector according to claim 4 wherein the charger is a universal serial bus charger having a charging port.

6. The portable combined carbon monoxide detector and smoke detector according to claim 4 further including a dynamo housing mounted to the suitcase housing base and a dynamo is disposed in the dynamo housing.

7. The portable combined carbon monoxide detector and smoke detector according to claim 6 further including a shaft and wherein the shaft is coupled to the dynamo, and a wheel connected to the shaft such that as the wheel rotates the shaft rotates causing the dynamo to generate electrical energy.

8. The portable combined carbon monoxide detector and smoke detector according to claim 7 further including a dynamo battery disposed in the suitcase housing and a wire connected to the dynamo and the dynamo battery such that electricity generated by the dynamo is delivered from the dynamo to the dynamo battery and stored in the dynamo battery.

9. The portable combined carbon monoxide detector and smoke detector according to claim 8 wherein the dynamo battery is wired to the charger and the charger has a charging port such that the charging port serves as a source of electrical for charging devices in need of electric energy.

10. The portable combined carbon monoxide detector and smoke detector according to claim 9 wherein the smoke detector and the carbon monoxide detector are powered by a battery, and a detector charger having a detector charging port is provided and the detector charger is mounted to the detector housing.

11. The portable combined carbon monoxide detector and smoke detector according to claim 10 wherein a cable is provide having opposed ends and each of the opposed ends has a connector and wherein one connector is plugged into the charging port of the charger mounted on the suitcase housing and the other connector is plugged into the detector charger port such that the dynamo battery is capable of charging the battery.

12. A method of detecting carbon monoxide and smoke comprising the acts of:
    providing a detector housing;
    providing a carbon monoxide detector and disposing the carbon monoxide detector in the detector housing;
    providing a smoke detector and disposing the smoke detector in the detector housing;
    providing a suitcase having a suitcase housing and a handle assembly supported by the suitcase housing and the handle assembly includes a handle with a handgrip portion and the handle having first and second slider arms that extend from the handgrip portion and mounting the detector housing on the first slider arm.

13. The method of detecting carbon monoxide and smoke according to claim 12 further including providing the suitcase housing with a housing base and an opposed suitcase housing end and connecting an electronic device pocket to the suitcase housing end and mounting a charger on the suitcase housing end.

14. The method of detecting carbon monoxide and smoke according to claim 13 further including providing a dynamo housing and mounting the dynamo housing to the suitcase housing base and disposing a dynamo the dynamo housing, and providing a shaft and coupling the shaft is coupled to the dynamo, and providing a wheel and connecting the wheel to the shaft such that as the wheel rotates the shaft rotates causing the dynamo to generate electrical energy, and providing a dynamo battery and mounting the dynamo battery to the suitcase housing and providing a wire and connecting the wire to the dynamo and the dynamo battery such that electricity generated by the dynamo is delivered from the dynamo to the dynamo battery, and wiring the dynamo battery to the charger and the charger has a charging port such that the charging port serves as a source of electrical for charging devices in need of electric energy.

15. The method of detecting carbon monoxide and smoke according to claim 14 further including powering the smoke detector and the carbon monoxide detector with a battery for powering the smoke and carbon monoxide detectors and providing a detector charger having a detector charging port and mounting the detector charger to the detector housing, and providing a cable having opposed ends and providing each end with a connector and plugging one end into the charging port of the charger mounted on the suitcase housing and plugging the other connector into the detector charger port and charging the battery with the dynamo battery.

* * * * *